United States Patent
Liu et al.

(10) Patent No.: US 12,161,494 B2
(45) Date of Patent: Dec. 10, 2024

(54) C-ARMS AND X-RAY DEVICES

(71) Applicant: SHANGHAI UNITED IMAGING HEALTHCARE CO., LTD., Shanghai (CN)

(72) Inventors: Wenqiang Liu, Shanghai (CN); Qiang Yu, Shanghai (CN); Baojian Wang, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 316 days.

(21) Appl. No.: 17/660,401

(22) Filed: Apr. 22, 2022

(65) Prior Publication Data
US 2022/0249043 A1    Aug. 11, 2022

Related U.S. Application Data

(63) Continuation of application No. PCT/CN2020/123015, filed on Oct. 22, 2020.

(30) Foreign Application Priority Data

Oct. 22, 2019 (CN) .......................... 201911004156.6
Nov. 21, 2019 (CN) .......................... 201911147705.5
Nov. 21, 2019 (CN) .......................... 201911147731.8

(51) Int. Cl.
*A61B 6/00* (2024.01)
*A61B 6/42* (2024.01)
(Continued)

(52) U.S. Cl.
CPC .......... *A61B 6/4441* (2013.01); *A61B 6/4275* (2013.01); *A61B 6/504* (2013.01); *B25J 9/047* (2013.01); *A61B 2090/3764* (2016.02)

(58) Field of Classification Search
CPC ..... A61B 6/4441; A61B 6/4275; A61B 6/504; A61B 2090/3764; A61B 6/4458; A61B 6/588; B25J 9/047
See application file for complete search history.

(56) References Cited

U.S. PATENT DOCUMENTS 5,050,204 A * 9/1991 Siczek ................. A61B 6/4464
378/197
7,905,658 B2    3/2011 Groβ et al.
(Continued)

FOREIGN PATENT DOCUMENTS

CN      101933813 A    1/2011
CN      202776337 U    3/2013
(Continued)

OTHER PUBLICATIONS

International Search Report in PCT/CN2020/123015 mailed on Jan. 21, 2021, 5 pages.
(Continued)

*Primary Examiner* — David P Porta
*Assistant Examiner* — Meenakshi S Sahu
(74) *Attorney, Agent, or Firm* — METIS IP LLC

(57) ABSTRACT

The present disclosure relates to a C-arm. The C-arm may include a connection component, a driving component, a first support component, and a second support component. The first support component may be configured to support a radiation generator. The second support component may be configured to support a radiation detector. The first support component and the second support may be movably connected to the connection component. The driving component may be configured to drive a movement of the first support component relative to the connection component.

20 Claims, 7 Drawing Sheets

(51) Int. Cl.
    *A61B 6/50*     (2024.01)
    *A61B 90/00*     (2016.01)
    *B25J 9/04*     (2006.01)

(56) References Cited

U.S. PATENT DOCUMENTS

| | | |
|---|---|---|
| 2001/0005410 A1 | 6/2001 | Rasche et al. |
| 2003/0112926 A1 | 6/2003 | Atzinger |
| 2008/0013690 A1 | 1/2008 | Lurz et al. |
| 2008/0037712 A1 | 2/2008 | Klingenbeck-Regn |
| 2008/0279340 A1 | 11/2008 | Grebner et al. |
| 2009/0180592 A1 | 7/2009 | Gross et al. |
| 2012/0300909 A1 | 11/2012 | Simmons et al. |
| 2013/0039464 A1 | 2/2013 | Tsujii et al. |
| 2017/0367667 A1 | 12/2017 | Hou |
| 2018/0333116 A1 | 11/2018 | Atzinger et al. |

FOREIGN PATENT DOCUMENTS

| | | |
|---|---|---|
| CN | 204269573 U | 4/2015 |
| CN | 105832362 A | 8/2016 |
| CN | 106725566 A | 5/2017 |
| CN | 207570504 U | 7/2018 |
| CN | 109009194 A | 12/2018 |
| CN | 109480878 A | 3/2019 |
| CN | 209032396 U | 6/2019 |
| CN | 110123350 A | 8/2019 |
| CN | 110811655 A | 2/2020 |
| CN | 110833426 A | 2/2020 |
| CN | 111227855 A | 6/2020 |
| JP | 2008099740 A | 5/2008 |
| JP | 2010213729 A | 9/2010 |

OTHER PUBLICATIONS

Written Opinion in PCT/CN2020/123015 mailed on Jan. 21, 2021, 6 pages.
First Office Action in Chinese Application No. 201911147705.5 mailed on Jan. 20, 2021, 23 pages.
First Office Action in Chinese Application No. 201911147731.8 mailed on Jan. 6, 2021, 16 pages.

\* cited by examiner

C-ARMS AND X-RAY DEVICES

CROSS-REFERENCE TO RELATED APPLICATIONS

This application is a continuation of International Application No. PCT/CN2020/123015, filed on Oct. 22, 2020, which claims priority to Chinese Patent Application No. 201911004156.6, filed on Oct. 22, 2019, Chinese Patent Application No. 201911147705.5, filed on Nov. 21, 2019, and Chinese Patent Application No. 201911147731.8, filed on Nov. 21, 2019, the contents of each of which are hereby incorporated by reference.

TECHNICAL FIELD

The present disclosure relates to the field of medical supplies, in particular, to a C-arm and an X-ray device.

BACKGROUND

A C-arm is a bracket with a C shape, which can be used to carry a device. For example, an X-radiation generator and an X-radiation detector may be disposed on the C-arm to be an X-ray illuminated component of an X-ray device. In some cases, the device disposed on the C-arm may need to be moved. For example, when the X-ray device with the X-radiation generator and the X-radiation detector is used, a distance between the X-radiation generator and the X-radiation detector may be adjusted. Generally, the C-arm is formed by combining sheet metal parts or castings. Therefore, it is desirable to provide a C-arm which could be effectively adjusted according to actual needs.

SUMMARY

According to an aspect of the present disclosure, a C-arm is provided. The C-arm may include a connection component, a driving component, a first support component, and a second support component. The first support component may be configured to support a radiation generator. The second support component may be configured to support a radiation detector. The first support component and the second support may be movably connected to the connection component. The driving component may be configured to drive a movement of the first support component relative to the connection component.

In some embodiments, the driving component may include a driving assembly. The driving assembly may be configured to drive the first support component and the second support component to move toward or away from each other.

In some embodiments, the driving assembly may drive the first support component to move at a first speed. The driving assembly may drive the second support component to move at a second speed. The first speed may be the same as the second speed.

In some embodiments, the driving assembly may drive the first support component to move at a third speed. The driving assembly may drive the second support component to move at a fourth speed. The third speed may be different from the fourth speed.

In some embodiments, a ratio of the third speed to the fourth speed may be equal to a ratio of weights of the second support component and one or more second units disposed on the second support component to weights of the first support component and one or more first units disposed on the first support component.

In some embodiments, a position of a center of gravity of the C-arm during movements of the first support component and the second support component relative to the connection component may be constant.

In some embodiments, the driving assembly may include a motor, a worm, a first rack, and a second rack. The motor may drive the worm to rotate, and an axis of the worm may be along the extending direction of the connection component. The worm may include a first spiral segment and a second spiral segment. A spiral direction of the first spiral segment may be opposite to a spiral direction of the second spiral segment. The first rack may be engaged with the first spiral segment and connected to the first connection component. The second rack may be engaged with the second spiral segment and connected to the second connection component.

In some embodiments, a lead of the first spiral segment may be different from a lead of the second spiral segment.

In some embodiments, the driving assembly may include a motor, a leadscrew, a first nut, and a second nut. The motor may drive the leadscrew to rotate along an axis of the leadscrew, and an axis of the leadscrew may be along the extending direction of the connection component. The leadscrew may include a third spiral segment and a fourth spiral segment, and a spiral direction of the third spiral segment may be opposite to a spiral direction of the fourth spiral segment. The first nut may be matched with the third spiral segment and connected to the first connection component. The second nut may be matched with the second spiral segment and connected to the second connection component.

In some embodiments, the driving assembly may include a motor, a gear, a third rack, and a fourth rack. The motor may drive the gear to rotate. The third rack and the fourth rack may be disposed along the direction of the extending direction of the connection component and mesh with the gear. The third rack may be connected to the first support component and the fourth rack may be connected to the second support component.

In some embodiments, the driving component may include a first driving unit and a second driving unit. The first driving unit may be configured to drive the first support component to move relative to the connection component. The second driving unit may be configured to drive the second support component to move relative to the connection component.

In some embodiments, the first support component may move relative to the connection component along a first route. The second support component may move relative to the connection component along a second route. The first route may be parallel to or collinear with the second route.

In some embodiments, the C-arm may include a controller. The controller may be configured to control the first driving unit to drive the first support component to move. The controller may be configured to control the second driving unit to drive the second support component to move.

In some embodiments, the controller may control the first support component to move relative to the connection component at a fifth speed. The controller may control the second support component to move relative to the connection component at a sixth speed. The fifth speed may be the same as the sixth speed.

In some embodiments, the controller may control the first support component to move relative to the connection component at a seventh speed. The controller may control the second support component to move relative to the connection component at an eighth speed. The seventh speed may be different from the eighth speed.

In some embodiments, a ratio of the seventh speed to the eighth speed may be equal to a ratio of weights of the second support component and one or more second units disposed on the second support component to weights of the first support component and one or more first units disposed on the first support component.

In some embodiments, a ratio of the seventh speed to the eighth speed may be such that a position of a center of gravity of the C-arm during movements of the first support component and the second support component relative to the connection component is constant.

In some embodiments, the first driving unit or the second driving unit may include a motor and at least one of a worm-rack drive, a gear-rack drive, a screw-nut drive, a belt drive, or a chain drive.

In some embodiments, at least one of the first support component, the second support component, or the connection component may include a chamber, and the driving component may be disposed in the chamber.

In some embodiments, the first support component and the second support component may be made of a material selected from carbon fiber, glass fiber, or metal fiber.

In some embodiments, one or more reinforcing ribs may be disposed on at least one of the first support component or the second support component.

According to another aspect of the present disclosure, an X-ray device is provided. The X-ray device may include a gantry, a radiation generator, a radiation detector, and the C-arm described according to some embodiments of the present disclosure. The connection component of the C-arm may be rotatably connected to the gantry.

In some embodiments, the gantry may include a robot arm.

In some embodiments, the X-ray device may include a digital subtraction angiography (DSA) device.

According to yet another aspect of the present disclosure, a C-arm is provided. The C-arm may include a connection component, a first support component, and a second support component. The first support component may be configured to support a radiation generator. The second support component may be configured to support a radiation detector. The first support component may be connected to a first end of the connection component. The second support component may be connected to a second end of the connection component. Each of the first support component and the second support component may be integrally formed of a material selected from carbon fiber, glass fiber, or metal fiber.

In some embodiments, the connection component may be integrally formed of carbon fiber.

In some embodiments, the connection component may include carbon fiber, and at least one of the first support component and the second support component may be integrally formed with the connection component.

In some embodiments, at least one of the first support component, the second support component, or the connection component may include a chamber.

In some embodiments, one or more reinforcing ribs may be disposed on at least one of the first support component or the second support component.

In some embodiments, the first support component may include a first connection unit, and the first connection unit may be connected to a radiation generator. The second support component may include a second connection unit, and the second connection unit may be connected to a radiation detector.

In some embodiments, the C-arm may further include a driving component. The driving component may be configured to drive at least one of the first support component and the second support component to move along a length direction of the connection component.

According to yet another aspect of the present disclosure, an X-ray device is provided. The X-ray device may include a gantry, a radiation generator, a radiation detector, and the C-arm described according to some embodiments of the present disclosure. The connection component of the C-arm may be connected to the gantry. The radiation generator may be disposed on the first support component of the C-arm. The radiation detector may be disposed on the second support component of the C-arm.

In some embodiments, the connection component of the C-arm may be rotatably connected to the gantry.

BRIEF DESCRIPTION OF THE DRAWINGS

The present disclosure is further illustrated in terms of exemplary embodiments. These exemplary embodiments are described in detail with reference to the drawings. These embodiments are non-limiting exemplary embodiments, in which like reference numerals represent similar structures, and wherein.

REFERENCE NUMERALS AND REPRESENTED STRUCTURES

Figure 1:
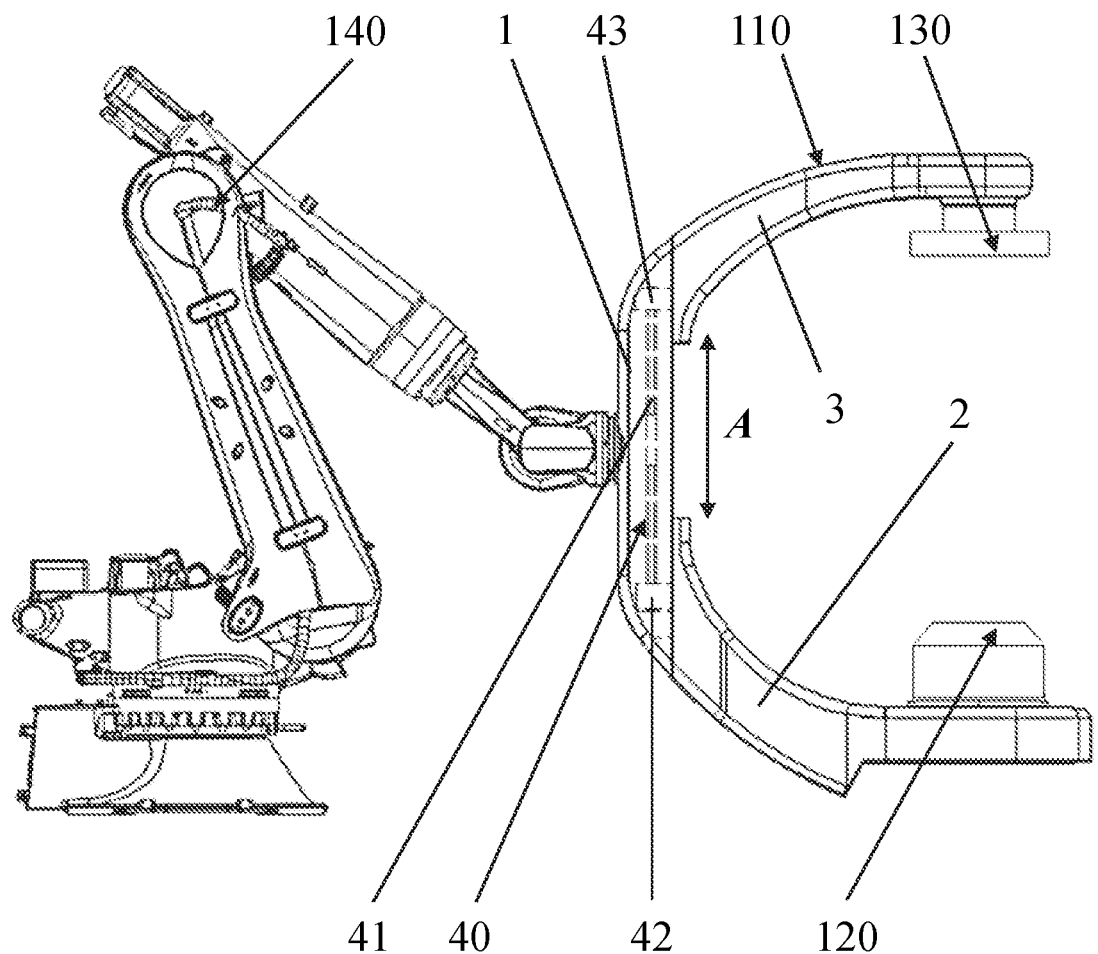
FIG. 1 is a schematic diagram illustrating an exemplary C-arm according to some embodiments of the present disclosure.

1000—X-ray device, 110—C-arm, 120—radiation generator, 130—radiation detector, 140—gantry, 1—connection component, 2—first support component, 21—first connection component, 3—second support component, 31—second connection component, 40—driving assembly, 41—leadscrew, 42—first nut, 43—second nut, 4—first driving unit, 5—second driving unit, and 6—chamber.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "unit," "module," and/or "block" used herein are one method to distinguish different components, elements, parts, sections, or assembly of different levels in ascending order. However, the terms may be displaced by another expression if they achieve the same purpose.

It will be understood that when a unit, engine, module, or block is referred to as being "on," "connected to," or "coupled to," another unit, engine, module, or block, it may be directly on, connected or coupled to, or communicate with the other unit, engine, module, or block, or an intervening unit, engine, module, or block may be present unless the context clearly indicates otherwise. As used herein, the term "and/or" includes any and all combinations of one or more of the associated listed items.

It will be understood that, although the terms "first," "second," "third," etc., may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention.

Spatial and functional relationships between elements (for example, between layers) are described using various terms, including "connected," "engaged," "interfaced," and "coupled." Unless explicitly described as being "direct," when a relationship between first and second elements is described in the present disclosure, that relationship includes a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

An aspect of the present disclosure provides a C-arm and an X-ray device. The C-arm may include a C-shaped bracket. The C-arm may drive a first support component and/or a second support component to move relative to a connection component via a driving component, thereby adjusting a distance between the first support component and the second support component of the C-arm. The C-arm can be applied to various occasions. For example, the C-arm may be used in a medical device such as an X-ray device, a computed tomography (CT) device, a linear accelerator, etc.

Figure 2:
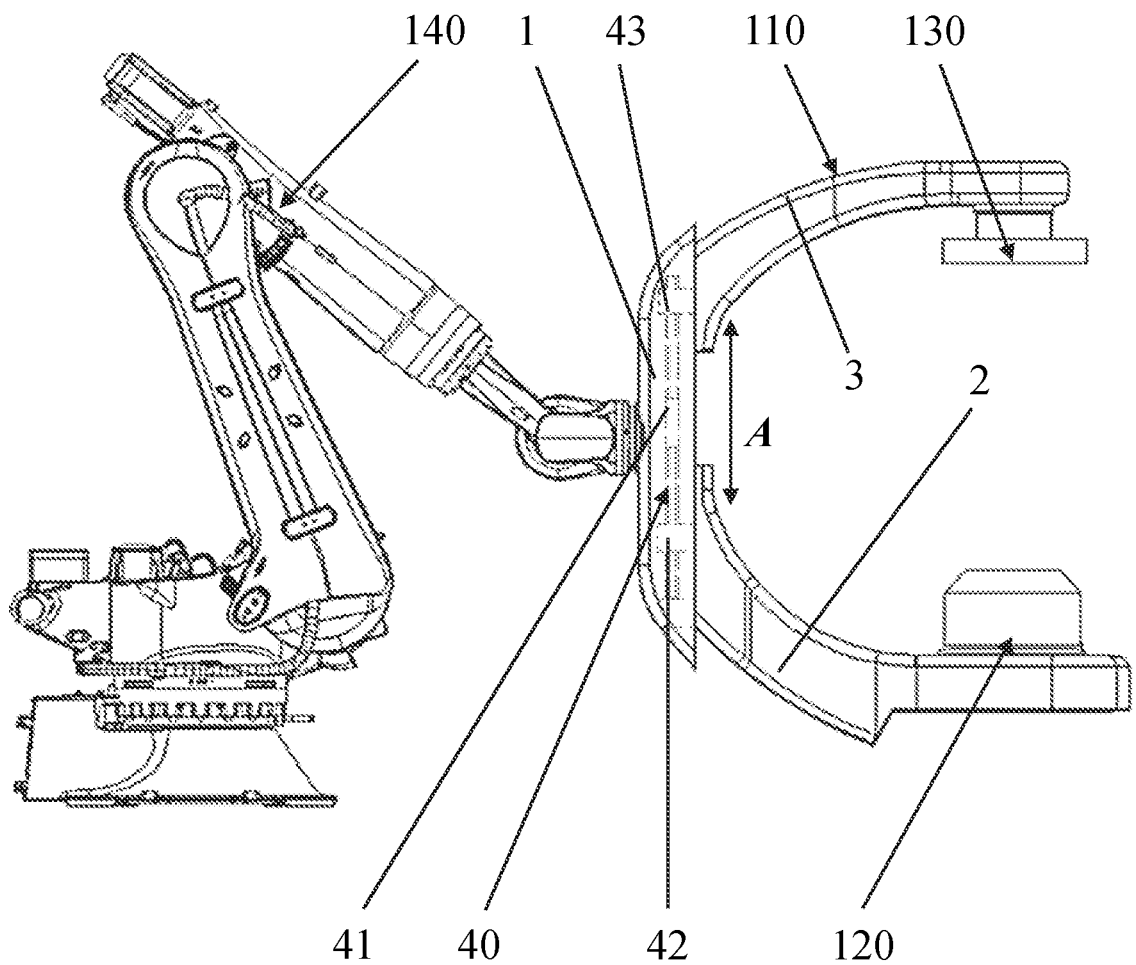
FIG. 2 is a schematic diagram illustrating an exemplary C-arm according to some embodiments of the present disclosure.
Figure 3:
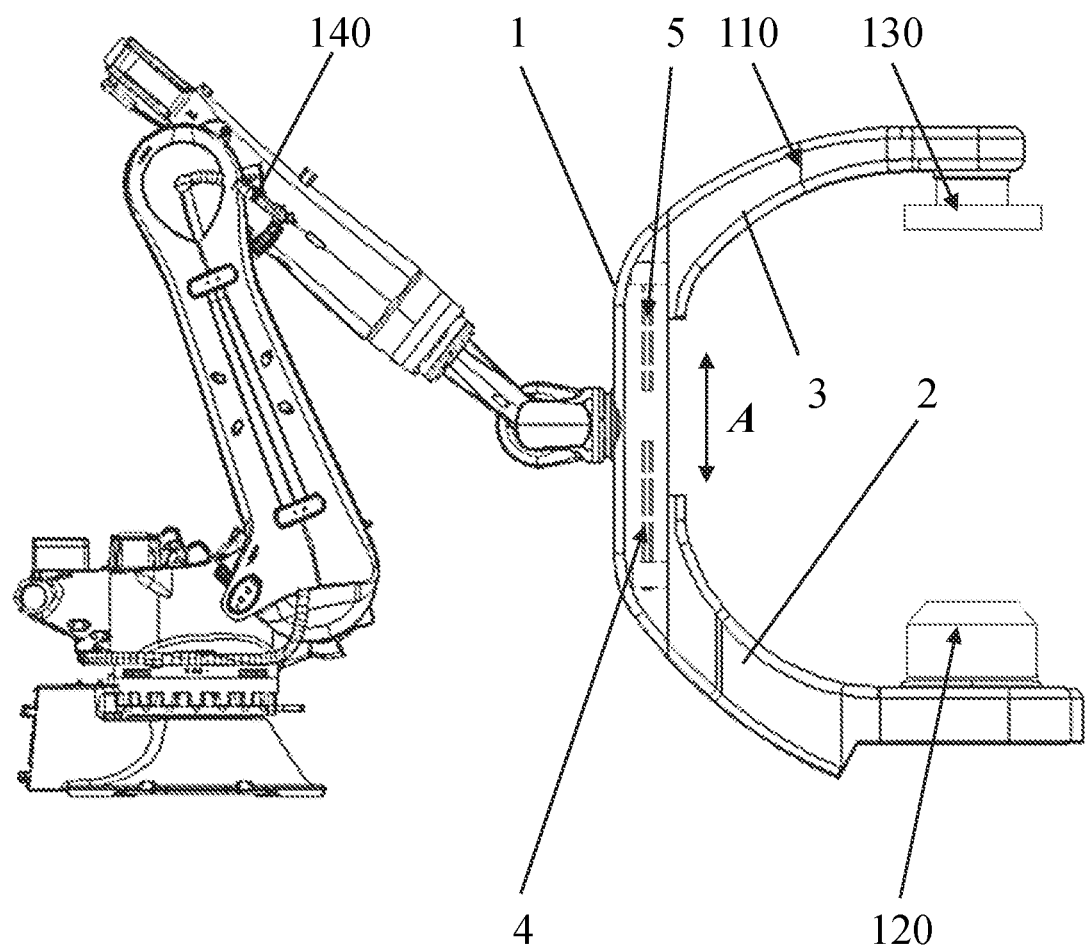
FIG. 3 is a schematic diagram illustrating an exemplary C-arm according to some embodiments of the present disclosure.
Figure 4:
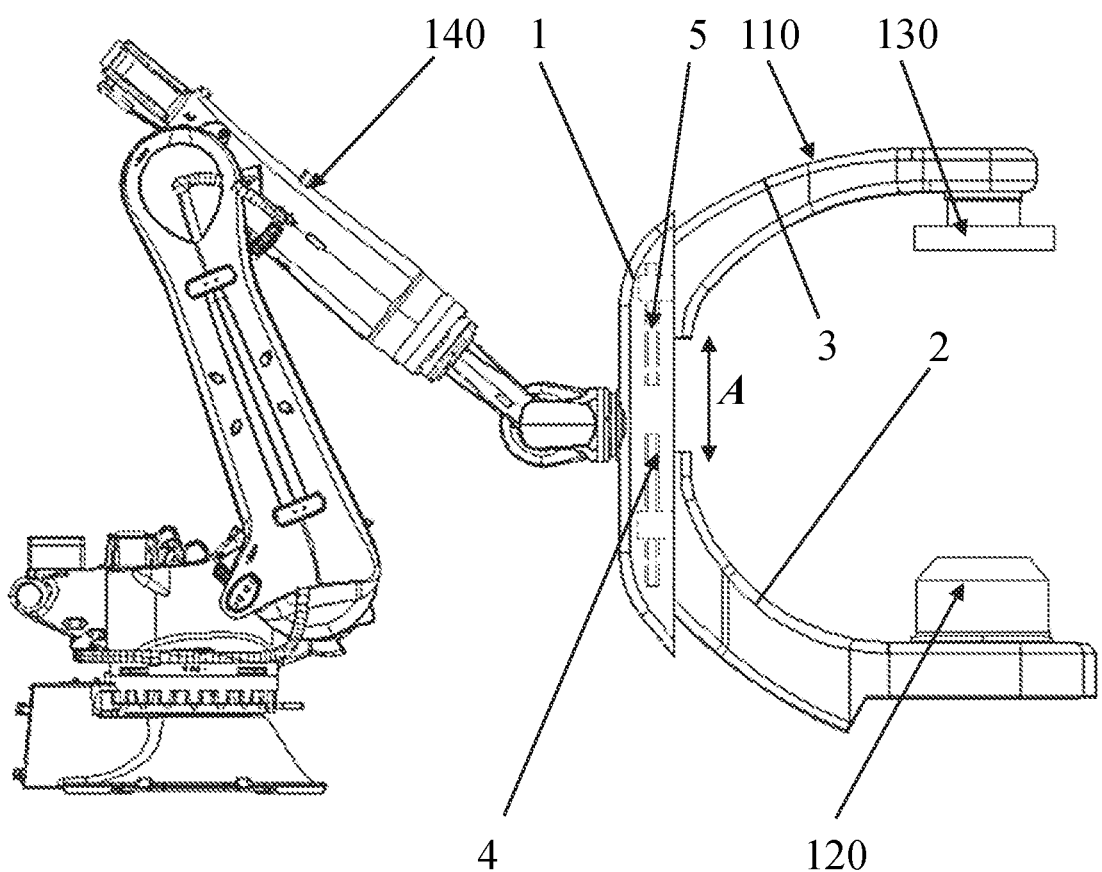
FIG. 4 is a schematic diagram illustrating an exemplary C-arm according to some embodiments of the present disclosure.

FIG. 1 is a schematic diagram illustrating an exemplary C-arm according to some embodiments of the present disclosure. FIG. 2 is a schematic diagram illustrating the C-arm as described in connection with FIG. 1, which may be in a state different from a state of the C-arm in FIG. 1. FIG. 3 is a schematic diagram illustrating an exemplary C-arm according to some embodiments of the present disclosure. FIG. 4 is a schematic diagram illustrating an exemplary C-arm according to some embodiments of the present disclosure. The C-arm 110 will be described in detail below.

In some embodiments, the driving component may include a driving assembly. As shown in FIG. 1, the C-arm 110 may include a connection component 1, a driving assembly 40, a first support component 2, and a second support component 3. The first support component 2 may be configured to support a radiation generator. The second support component 3 may be configured to support a radiation detector. The first support component 2 and the second support component 3 may be movably connected to the connection component 1. The driving assembly 40 may be configured to drive the first support component 2 and the second support component 3 to move toward or away from each other along an extending direction of the connection component 1. The extending direction of the connection component 1 refers to a length direction of the connection component 1 indicated by the arrow A in FIG. 1 and FIG. 2. As shown in FIG. 1, the first support component 2 and the second support component 3 may be disposed on two ends of the connection component 1, respectively. The first support component 2, the second support component 3, and the connection component 1 may form a C shape. A distance between a radiation generator 120 and a radiation detector 130 may be adjusted when the first support component 2 and/or the second support component 3 moves along the extending direction of the connection component 1. FIG. 2 is a schematic diagram illustrating the X-ray device 1000 when the first support component 2 and the second support component 3 move toward each other from a state as described in connection with FIG. 1 according to some embodiments of the present disclosure. The radiation generator 120 refers to a device that can emit rays (e.g., X-rays, gamma rays, electronic rays, etc.). The radiation detector 130 refers to a device that can receive the rays emitted by the radiation generator 120. Through the cooperation of the radiation generator 120 and the radiation detector 130, one or more operations such as a medical examination or a medical treatment may be performed. In some embodiments, the connection component 1 may include a sliding groove along the extending direction of the connection component 1. At least one of the first support component 2 and the second support component 3 may include a sliding block, the sliding block may slide along the sliding groove, and accordingly, the first support component 2 and the second support component 3 may move along the extending direction of the connection component 1.

In the application of the C-arm 110, a carrying mechanism (e.g., a gantry of an X-ray device, a gantry of a CT device, a gantry of a linear accelerator, etc.) may be configured to carry the C-arm 110 and connected to a center of the connection component 1. The C-arm 110 may move (e.g., rotate) relative to the carrying mechanism. The movement of the first support component 2 and the second support component 3 toward or away from each other along the extending direction of the connection component 1 may reduce a load (e.g., a torque applied by the C-arm to the carrying mechanism), a load change (e.g., a change of the center of gravity of the C-arm 110), etc., of the carrying mechanism when the first support component 2 and the second support component 3 moves, thereby improving the stability of the C-arm 110, the stability of the carrying mechanism, and the service life of the C-arm 110 and/or the X-ray device 1000.

In some embodiments, a speed (also referred to as the speed of the first support component 2) at which the first support component 2 moves along the connection component 1 and a speed (also referred to as a speed of the second support component 3) at which the second support component 3 moves along the connection component 1 may be the same.

In some embodiments, the speed of the first support component 2 may be greater than the speed of the second support component 3. For example, the driving assembly 40 may be configured such that the speed of the first support component 2 is greater than the speed of the second support component 3. In some embodiments, a weight of the radiation generator 120 may be greater than a weight of the radiation detector 130. For example, the weight of the radiation generator 120 may be 100 Kg-120 Kg, and the weight of the radiation detector 130 may be 30 Kg-40 Kg. Weights of the first support component 2 and one or more first units disposed on the first support component 2 may be greater than weights of the second support component 3 and one or more second units disposed on the second support component 3. During the use of the C-arm 110, when the C-arm 110 is in an initial state, the first support component 2 and the second support component 3 may be located at two ends of the connection component 1, respectively, thereby improving an operation space between the radiation generator 120 and the radiation detector 130. The first support component 2 and the second support component 3 may be moved towards each other, and the first support component 2 and the second support component 3 may be moved to pre-determined positions, respectively. Since the weight of the radiation generator 120 is greater than the weight of the radiation detector 130, the center of gravity of the C-arm 110 may deviate from a central axis of rotation of the C-arm 110 and the carrying mechanism may receive a relatively great torque when the first support component 2 and the second support component 3 are disposed symmetrically with the central axis of the rotation of the C-arm 110. When the speed of the first support component 2 is greater than the speed of the second support component 3, the center of gravity of the C-arm 110 may be close to the central axis of rotation of the C-arm 110, the torque received by the carrying mechanism may be reduced, and the load carried by the carrying mechanism may be reduced during adjusting the distance between the first support component 2 and the second support component 3 from the initial state of the C-arm 110.

In some embodiments, a ratio of the speed of the first support component 2 to the speed of the second support component 3 may be any value greater than 1. For example, the ratio of the speed of the first support component 2 to the speed of the second support component 3 may be 2:1, 3:1, 5:1, etc. In some embodiments, the ratio of the speed of the first support component 2 to the speed of the second support component 3 may be equal to a ratio of weights of the first support component 2 and the one or more first units disposed on the first support component 2 to weights of the second support component 3 and the one or more second units disposed on the second support component 3. Merely by way of example, the weights of the first support component 2 and the one or more first units disposed on the first support component 2 are 120 Kg, and the weights of the second support component 3 and the one or more second units disposed on the second support component 3 are 40 Kg. The ratio of the speed of the first support component 2 to the speed of the second support component 3 is equal to 3:1. It should be noted that the weights of the first support component 2 and the one or more first units disposed on the first support component 2 refers to a sum of a weight of the first support component 2 and weights of the one or more first units disposed on the first support component 2. The weights of the second support component 3 and the one or more second units disposed on the second support component 3 refers to a sum of a weight of the second support component 3 and weights of the one or more second units disposed on the second support component 3. In some embodiments, when the weights of the first support component 2 and the second support component 3 are the same (or substantially the same), the ratio of the speed of the first support component 2 to the speed of the second support component 3 may be equal to (or substantially equal to) a ratio of a weight of the radiation generator 120 to a weight of the radiation detector 130.

In some embodiments, the speed of the first support component 2 may be less than the speed of the second support component 3. For example, the driving assembly 40 may be configured such that the speed of the first support component 2 is less than the speed of the second support component 3. Since the weights of the first support component 2 and the one or more first units disposed on the first support component 2 are greater than the weights of the second support component 3 and the one or more second units disposed on the second support component 3, during the movements of the first support component 2 and the second support component 3, a change of the center of gravity of the C-arm 110 may be relatively small compared to the center of gravity of the C-arm 110 when the C-arm 110 is in the initial state. For instance, the change of the center of gravity of the C-arm 110 may be in a range of 0.1-5 cm (e.g., 0.1 cm, 0.5 cm, 1 cm, 3 cm, 5 cm) compared to the center of gravity of the C-arm 110 when the C-arm 110 is in the initial state. In some embodiments, the ratio of the speed of the first support component 2 to the speed of the second support component 3 may be any value less than 1. For example, the ratio of the speed of the first support component 2 to the speed of the second support component 3 may be 1:2, 1:3, 2:5, etc. As another example, the ratio of the speed of the first support component 2 to the speed of the second support component 3 may be equal to the ratio of the weight of the radiation detector 130 to the weight of the radiation generator 120.

In some embodiments, during the movement of the first support component 2 relative to the connection component 1 and the movement of the second support component 3 relative to the connection component 1, a position of the center of gravity of the C-arm 110 may be (essentially) unchanged. Those skilled in the art may determine the speed of the first support component 2 and the speed of the second support component 3 based on the weights of the first support component 2 and the one or more first units disposed on the first support component 2, the weights of the second support component 3 and the one or more second units disposed on the second support component 3, and a weight of the connection component 1, thereby remaining the position of the center of gravity of the C-arm 110 (essentially) unchanged. For example, the ratio of the speed of the first support component 2 to the speed of the second support component 3 may be equal to the ratio of the weights of the second support component 3 and the one or more second units disposed on the second support component 3 to the weights of the first support component 2 and the one or more first units disposed on the first support component 2. In this case, the position of the center of gravity of the C-arm 110 may be (essentially) unchanged during the movements of the first support component 2 and the second support component 3. Merely by way of example, the weights of the first support component 2 and the one or more first units disposed on the first support component 2 are 120 Kg, and the weights of the second support component 3 and the one or more second units disposed on the second support component 3 are 40 Kg. The ratio of the speed of the first support component 2 to the speed of the second support component 3 is equal to 1:3. The position of the center of gravity of the C-arm 110 may be (essentially) unchanged by setting the ratio of the speed of the first support component 2 to the speed of the second support component 3, the effect of the change of the center of gravity of the C-arm 110 to the load of the C-arm 110 and the carrying mechanism may be not considered during a design and/or manufacture process of the C-arm 110, and the difficulty of controlling the movement of the C-arm 110 may be reduced. In some alternative embodiments, when the C-arm rotates relative to the carrying mechanism of the C-arm 110, the center of gravity of the C-arm may coincide with a rotation axis of the C-arm 110, thereby reducing the load of the carrying mechanism. For example, the rotation axis of the carrying mechanism of the C-arm 110 may be set at a position that coincides with the center of gravity of the C-arm 110.

In some embodiments, the driving assembly 40 may include a motor, a worm, a first rack, and a second rack. The motor may drive the worm to rotate along an axis of the worm. The axis of the worm may be along the extending direction of the connection component 1. The worm may include a first spiral segment and a second spiral segment. A spiral direction of the first spiral segment may be opposite to a spiral direction of the second spiral segment. The first rack may be engaged with the first spiral segment and connected to the first connection component 2. The second rack may be engaged with the second spiral segment and connected to the second connection component 3. A movement direction of the first rack may be opposite to a movement direction of the second rack, and a movement direction of the first support component 2 may be opposite to a movement direction of the second support component 3. In some embodiments, the worm may be rotatably disposed on the connection component 1. In addition, the motor may be connected to the worm via a reducer. The movements of the first support component 2 and the second support component 3 may be driven by matching the worm and the rack, thereby improving the driving ratio, driving stability of the driving assembly 40, and reducing noise.

In some embodiments, a lead of the first spiral segment and a lead of the second spiral segment may be the same, so that the speed of the first support component 2 may be the same as the speed of the second support component 3. In some embodiments, the lead of the first spiral segment may be different from the lead of the second spiral segment. For example, the lead of the first spiral segment may be greater than the lead of the second spiral segment, and accordingly, the speed of the first support component 2 may be greater than the speed of the second support component 3. As another example, the lead of the first spiral segment may be less than the lead of the second spiral segment, and accordingly, the speed of the first support component 2 may be less than the speed of the second support component 3. Those skilled in the art may determine the lead of the first spiral segment and the lead of the second spiral segment according to the ratio of the speed of the first support component 2 to the speed of the second support component 3 as needed, which is not limited in the present disclosure.

As shown in FIG. 1 and FIG. 2, in some embodiments, the driving assembly 40 may include a motor, a leadscrew 41, a first nut 42, and a second nut 43. The motor may drive the leadscrew 41 to rotate along an axis of the leadscrew 41. The axis of the leadscrew 41 may be along the extending direction of the connection component 1. The leadscrew 41 may include a third spiral segment and a fourth spiral segment. A spiral direction of the third spiral segment may be opposite to a spiral direction of the fourth spiral segment. The first nut may be matched with the third spiral segment and connected to the first support component 2. The second nut may be matched with the second spiral segment and connected to the second support component 3. A movement direction of the first nut 42 and a movement direction of the second nut 43 may be opposite to each other during the rotation of the leadscrew 41, so that the first support component 2 and the second support component 3 may move in opposite directions. In some embodiments, the leadscrew 41 may be rotatably disposed on the connection component 1. In some embodiments, the motor may be connected to the leadscrew 41 via a reducer. In some embodiments, the motor may include a direct drive motor. The leadscrew 41 may be together with the nut (e.g., the first nut 42, the second nut 43, etc.) to drive the movement of the first support component 2 and the movement of the second support component 3, thereby improving the driving efficiency and driving accuracy of the driving assembly 40, and improving the convenience of adjusting the distance between the radiation generator 120 and radiation detector 130.

In some embodiments, the lead of the first spiral segment and the lead of the second spiral segment may be the same, and accordingly, the speed of the first support component 2 may be the same as the speed of the second support component 3. In some embodiments, the lead of the first spiral segment may be different from the lead of the second spiral segment. For example, the lead of the first spiral segment may be greater than the lead of the second spiral segment, and accordingly, the speed of the first support component 2 may be greater than the speed of the first support component 2. As another example, the lead of the first spiral segment may be less than the lead of the second spiral segment, and accordingly, the speed of the first support component 2 may be less than the speed of the second support component 3.

In some embodiments, the driving assembly 40 may include a motor, a gear, a third rack, and a fourth rack. The motor may drive the gear to rotate. The gear may be rotatably connected to the connection component 1. The third rack and the fourth rack may be disposed along the extending direction of the connection component 1 and mesh with the gear. The third rack may be connected to the first support component 2 and the fourth rack may be connected to the second support component 3. The third rack and the fourth rack may be disposed on two sides of the gear, respectively. When the gear rotates, the third rack and the fourth rack may move in opposite directions, so that the first support component 2 and the second support component 3 may move in the opposite direction. The above mentioned gear-rack drive in which a rack (e.g., the third rack, a fourth rack, etc.) meshes with the gear to drive the movements of the first support component 2 and the second support component 3 may be applied to a scenario that the speed of the first support component 2 is the same as the speed of the second support component 3. In some embodiments, a gear set and a rack may be configured for driving the movements of the first support component 2 and the second support component 3. For example, a gear with a relatively great size and a gear with a relatively small size may rotate coaxially, or two gears with different modulus may rotate coaxially, and the two gears may be configured to drive the third rack and the fourth rack to move, respectively, so that the first support component 2 and the second support component 3 may move at different speeds. The gear-rack drive may improve the load of the C-arm 110, the driving speed, and efficiency of adjusting the distance between the radiation generator 120 and radiation detector 130, thereby improving the efficiency of performing a medical examination and/or a medical treatment. In some alternative embodiments, the driving assembly 40 may also include a belt drive (e.g., a synchronous belt drive), a chain drive, etc.

In some embodiments, the driving component may include a first driving unit and a second driving unit. As shown in FIG. 3, a C-arm 110 may include a connection component 1, a first driving unit 4, a first support component 2, a second driving unit 5, and a second support component 3. The first support component 2 may be configured to support a radiation generator 120. The second support component 3 may be configured to support a radiation detector 130. The first support component 2 and the second support component 3 may be movably connected to the connection component 1. The first driving unit 4 may be configured to drive the first support component 2 to move relative to the connection component 1. The second driving unit 5 may be configured to drive the second support component 3 to move relative to the connection component 1. As shown in FIG. 3, the first support component 2 and the second support component 3 may be disposed on two ends of the connection component 1, respectively, and the first support component 2, the second support component 3, and the connection component 1 may form a C shape. A distance between the radiation generator 120 and the radiation detector 130 may be adjusted when the first support component 2 and/or the second support component 3 move along the extending direction of the connection component 1. FIG. 4 is a schematic diagram illustrating the X-ray device when the first support component 2 and the second support component 3 move toward each other from a state as described in connection with FIG. 3 according to some embodiments of the present disclosure. The radiation generator 120 refers to a device that can emit rays (e.g., X-rays, gamma rays, electronic rays, etc.). The radiation detector 130 refers to a device that can receive the rays emitted by the radiation generator 120. Through the cooperation of the radiation generator 120 and the radiation detector 130, one or more operations such as medical examination or medical treatment may be performed. In some embodiments, the connection component 1 may include a first sliding groove. The first support component 2 may include a first sliding block, and the first sliding block may slide along the first sliding groove. The connection component 1 may include a second sliding groove. The second support component 3 may include a second sliding block, and the second sliding block may slide along the second sliding groove. The first support component 2 may move relative to the connection component 1, and the second support component 3 may move relative to the connection component 1. During the application of the C-arm 110, the distance between the first support component 2 and the second support component 3 of the C-arm 110 may be flexibly adjusted, thereby improving the convenience and efficiency of performing an operation such as a medical examination or a medical treatment on a patient performed by an operator of a device using the C-arm 110 (e.g., an X-ray device, a CT device, a linear accelerator, etc.).

In some embodiments, the first support component 2 may move relative to the connection component 1 along a first route. The second support component 3 may move relative to the connection component 1 along a second route. The first route may be parallel or collinear with the second route. For example, the first route may include a route where the first sliding block may slide along the first sliding groove, and the second route may include where the second sliding block may slide along the second sliding groove. In some embodiments, each of an extension direction of the first route and an extension direction of the second route may be the same as an extension direction of the connection component 1. In some embodiments, when the first route and the second route are collinear, the first route and the second route may be the same.

In some embodiments, the C-arm 110 may include a controller (not shown in the figure). The controller may be configured to control the first driving unit 4 to drive the first support component 2 to move, and/or the controller may be configured to control the second driving unit 5 to drive the second support component 3 to move. For example, the controller may control the first support component 2 and the second support component 3 to move independently. As another example, the controller may control the first support component 2 and the second support component 3 to move along a same direction. As yet another example, the controller may control the first support component 2 and the second support component 3 to move toward or away from each other. For example, the controller may control the first support component 2 to move and control the second support component 3 not to move, or vice versa. In some embodiments, the controller may be disposed within the C-arm 110 or a gantry 140. In some embodiments, the controller may include an independent device and be connected to the C-arm 110 via a signal connection (e.g., an electrical connection, a wireless connection, etc.). It should be noted that the controller may be implemented by a hardware, a software, or the like, or any combination thereof. The hardware may be implemented by using specific logic circuits. The software may be stored in a storage and may be executed by an appropriate instruction execution system, such as a microprocessor or a specifically designed hardware. It will be appreciated by those skilled in the art that the above methods and systems may be implemented by computer-executable instructions and/or control codes embedding in the controller. For example, the control codes may be provided by a medium such as a disk, a CD or a DVD-ROM, a programmable memory device such as a read-only memory (a firmware), or a data carrier such as an optical or electric signal carrier. The controller of the present disclosure may be implemented by hardware circuits, for example, very large scale integrated circuits or gate arrays, semiconductors such as logic chips or transistors, programmable hardware devices such as field-programmable gate arrays or programmable logic devices, etc. The controller may be implemented by software executed by various processors. The controller may also be implemented by a combination (e.g., firmware) of the hardware circuits and the software.

In some embodiments, the controller may be configured to control the speed of the first support component 2 relative to the connection component 1 to be equal to the speed of the second support component 3 relative to the connection component 1.

In some embodiments, the controller may be configured to control the speed of the first support component 2 relative to the connection component 1 to be greater than the speed of the second support component 3 relative to the connection component 1.

In some embodiments, a weight of the radiation generator 120 may be greater than a weight of the radiation detector 130. For example, the weight of the radiation generator 120 may be 100 Kg-120 Kg, and the weight of the radiation detector 130 may be 30 Kg-40 Kg. Weights of the first support component 2 and one or more first units disposed on the first support component 2 may be greater than weights of the second support component 3 and one or more second units disposed on the second support component 3. In the application of the C-arm 110, a carrying mechanism (e.g., a gantry of an X-ray device, a gantry of a CT device, a gantry of a linear accelerator, etc.) may be configured to carry the C-arm 110 and connected to a center of the connection component 1. The C-arm 110 may move (e.g., rotate) relative to the carrying mechanism. During the use of the C-arm 110, when the C-arm 110 is in an initial state, the first support component 2 and the second support component 3 may be located on two ends of the connection component 1, respectively, thereby improving an operation space between the radiation generator 120 and the radiation detector 130. The controller may control the first driving unit 4 to drive the first support component 2 to move, and/or the controller may control the second driving unit 5 to drive the second support component 3 to move. The first support component 2 and the second support component 3 may be moved towards each other, and the first support component 2 and the second support component 3 may be moved to pre-determined positions, respectively. Since the weight of the radiation generator 120 is greater than the weight of the radiation detector 130, the center of gravity of the C-arm 110 may deviate from a central axis of a rotation of the C-arm 110 and the carrying mechanism may receive a relative great torque when the first support component 2 and the second support component 3 are disposed symmetrically with the central axis of the rotation of the C-arm 110. When the speed of the first support component 2 is greater than the speed of the second support component 3, the center of gravity of the C-arm 110 may be close to the central axis of rotation of the C-arm 110, the torque received by the carrying mechanism may be reduced, and the load carried by the carrying mechanism may be reduced when the distance between the first support component 2 and the second support component 3 is adjusted from the initial state of the C-arm 110.

In some embodiments, a ratio of a movement speed of the first support component 2 relative to the connection component 1 to a movement speed of the second support component 3 relative to the connection component 1 may be any value greater than 1. For example, the ratio of the movement speed of the first support component 2 relative to the connection component 1 to the movement speed of the second support component 3 relative to the connection component 1 may be 2:1, 3:1, 5:1, etc. In some embodiments, the ratio of the movement speed of the first support component 2 relative to the connection component 1 to the movement speed of the second support component 3 relative to the connection component 1 may be equal to (or substantially equal to) a ratio of weights of the second support component 3 and one or more second units disposed on the second support component 3 to weights of the first support component 2 and one or more first units disposed on the first support component 2. Merely by way of example, the weights of the first support component 2 and the one or more first units disposed on the first support component 2 are 120 Kg, and the weights of the second support component 3 and the one or more second units disposed on the second support component 3 are 40 Kg. The ratio of the movement speed of the first support component 2 relative to the connection component 1 to the movement speed of the second support component 3 relative to the connection component 1 is equal to 3:1. It should be noted that the weights of the first support component 2 and the one or more first units disposed on the first support component 2 refers to a sum of a weight of the first support component 2 and weights of the one or more first units disposed on the first support component 2. The weights of the second support component 3 and the one or more second units disposed on the second support component 3 refers to a sum of a weight of the second support component 3 and weights of the one or more second units disposed on the second support component 3. In some embodiments, when the weights of the first support component 2 and the second support component 3 are the same (or substantially the same), the ratio of the speed of the first support component 2 to the speed of the second support component 3 may be equal to (or substantially equal to) a ratio of the weight of the radiation generator 120 to the weight of the radiation detector 130.

In some embodiments, the movement speed of the first support component 2 relative to the connection component 1 may be less than the movement speed of the second support component 3 relative to the connection component 1. Since the weights of the first support component 2 and the one or more first units disposed on the first support component 2 are greater than the weights of the second support component 3 and the one or more second units disposed on the second support component 3, during the movements of the first support component 2 and the second support component 3, a change of the center of gravity of the C-arm 110 may be relatively small compared to the center of gravity of the C-arm 110 when the C-arm 110 is in the initial state. For instance, the change of the center of gravity of the C-arm 110 may be in a range of 0.1-5 cm (e.g., 0.1 cm, 0.5 cm, 1 cm, 3 cm, 5 cm) compared to the center of gravity of the C-arm 110 when the C-arm 110 is in the initial state. In some embodiments, the ratio of the movement speed of the first support component 2 relative to the connection component 1 to the movement speed of the second support component 3 relative to the connection component 1 may be any value less than 1. For example, the controller may control that the ratio of the movement speed of the first support component 2 relative to the connection component 1 to the movement speed of the second support component 3 relative to the connection component 1 is 1:2, 1:3, 2:5, etc. As another example, the controller may control that the ratio of the movement speed of the first support component 2 relative to the connection component 1 to the movement speed of the second support component 3 relative to the connection component 1 is equal to the ratio of the weight of the radiation detector 130 to the weight of the radiation generator 120.

In some embodiments, during the movement of the first support component 2 relative to the connection component 1 and the movement of the second support component 3 relative to the connection component 1, the controller may control the ratio of the movement speed of the first support component 2 relative to the connection component 1 and the movement speed of the second support component 3 relative to the connection component 1 such that a position of the center of gravity of the C-arm 110 may be (essentially) unchanged. Those skilled in the art may determine the movement speed of the first support component 2 relative to the connection component 1 and the movement speed of the second support component 3 relative to the connection component 1 based on the weights of the first support component 2 and the one or more first units disposed on the first support component 2, the weights of the second support component 3 and the one or more second units disposed on the second support component 3, and a weight of the connection component 1, thereby remaining the position of the center of gravity of the C-arm 110 (essentially) unchanged. For example, the controller may control that the ratio of the movement speed of the first support component 2 relative to the connection component 1 to the movement speed of the second support component 3 relative to the connection component 1 is equal to the ratio of the weights of the second support component 3 and the one or more second units disposed on the second support component 3 to the weights of the first support component 2 and the one or more first units disposed on the first support component 2. In this case, the position of the center of gravity of the C-arm 110 may be (essentially) unchanged during the movements of the first support component 2 and the second support component 3. Merely by way of example, the weights of the first support component 2 and the one or more first units disposed on the first support component 2 are 120 Kg, and the weights of the second support component 3 and the one or more second units disposed on the second support component 3 are 40 Kg. The controller may control that the ratio of the movement speed of the first support component 2 relative to the connection component 1 to the movement speed of the second support component 3 relative to the connection component 1 is equal to 1:3. The position of the center of gravity of the C-arm 110 may be (essentially) unchanged by setting the ratio of the movement speed of the first support component 2 relative to the connection component 1 to the movement speed of the second support component 3 relative to the connection component 1, the effect of a change of the center of gravity of the C-arm 110 to the load of the C-arm 110 and the carrying mechanism may be not considered during a design and/or manufacture process of the C-arm 110, and the difficulty of controlling the movement of the C-arm 110 may be reduced. In some alternative embodiments, when the C-arm rotates relative to the carrying mechanism of the C-arm 110, the center of gravity of the C-arm may coincide with a rotation axis of the C-arm 110, thereby reducing the load of the carrying mechanism. For example, the rotation axis of the carrying mechanism of the C-arm 110 may be set at a position that coincides with the center of gravity of the C-arm 110.

In some embodiments, the first driving unit 4 and/or the second driving unit 5 may include a motor and a driving subunit. In some embodiment, the motor may include a direct drive motor. The driving subunit may include but is not limited to a worm-rack drive, a gear-rack drive, a screw-nut drive, a belt drive, a chain drive, or the like, or any combination thereof. The driving subunit of the first driving unit 4 may be connected between the motor of the first driving unit 4 and the first support component 2, and the driving subunit of the second drive unit 5 may be connected between the motor of the second driving unit 5 and the second support component 3. A type of the first driving unit 4 and that of the second driving unit 5 may be the same or different. For example, the first driving unit 4 may include a worm-rack drive, and the second driving unit 5 may include a gear-rack drive. As another example, each of the first driving unit 4 and the second driving unit 5 may include a screw-nut drive. In some alternative embodiments, the first driving unit 4 and/or the second driving unit 5 may include a hydraulic cylinder, a pneumatic cylinder, etc.

In some embodiments, the C-arm 110 may include a gravity center measurement component and a gravity center adjustment component. The gravity center measurement component and the gravity center adjustment component may be communicated with the controller. The gravity center measurement component may be configured to measure position information associated with the center of gravity of the C-arm 110 relative to a fixed object (e.g., a gantry). The gravity center measurement component may send the position information associated with the center of gravity of the C-arm 110 to the controller. The controller may determine whether the position of the center of gravity of the C-arm 110 is changed based on the position information. When the controller determines that the position of the center of gravity of the C-arm 110 is changed, the controller may adjust the position of the center of gravity of the C-arm 110 via the gravity center adjustment component. In some embodiments, the controller may determine whether the change of the position of the center of gravity of the C-arm 110 is within a preset range (e.g., a present distance). When the change of the position of the center of gravity is within the preset range, the controller may not adjust the position of the center of gravity of the C-arm 110. In some embodiments, the controller may determine a position of a rotation axis of the carrying mechanism of the C-arm 110 as a standard center of gravity position of the C-arm 110. The controller may compare a current position of the center of gravity of the C-arm 110 with the position of the standard center of gravity to determine whether to adjust the position of the center of gravity of the C-arm 110. For example, when the current position of the center of gravity of the C-arm 110 is different from the position of the standard center of gravity or a distance between the current position of the center of gravity of the C-arm 110 and the position of the standard center of gravity is greater than a distance threshold, the controller may determine that the position of the center of gravity of the C-arm 110 needs to be adjusted. As another example, when the current position of the center of gravity of the C-arm 110 coincides with the position of the standard center of gravity, or when the distance between the current position of the center of gravity of the C-arm 110 and the position of the standard center of gravity is less than the distance threshold, the controller may determine that the position of the center of gravity of the C-arm 110 does not need to be adjusted. In some embodiments, when the controller determines that the position of the center of gravity of the C-arm 110 needs to be adjusted, the controller may generate a gravity center adjustment instruction and send the gravity center adjustment instruction to the gravity center adjustment component. The gravity center adjustment component may adjust the center of gravity of the C-arm 110 such that the position of the center of gravity coincides with the position of the standard center of gravity or the distance between the position of the center of gravity and the position of the standard center of gravity is not greater than the distance threshold. In some embodiments, the gravity center adjustment component may control the ratio of the movement speed of the first support component 2 relative to the connection component 1 to the movement speed of the second support component 3 relative to the connection component 1 to adjust the position of the center of gravity of the C-arm 110. In some embodiments, the center of gravity adjusting component may include the first driving unit 4 and the second driving unit 5.

In some embodiments, the C-arm 110 may include a lifting assembly. The lifting assembly may be disposed between the connection component 1 and a support component (e.g., the first support component 2, the second support component 3, etc.). The driving component may drive the lifting assembly to move up and down. The movement of the lifting assembly may drive the support component to move along the extension direction of the connection component 1. In some embodiments, the lifting assembly may include a first lifting unit connected to the connection component 1, a second lifting unit connected to the support component, and a middle lifting unit connected to the first lifting unit and the second lifting unit. In some embodiments, the driving component may drive the middle lifting unit to move relative to the first lifting unit. In some embodiments, the driving component may drive the second lifting unit to move relative to the middle lifting unit. Each of the middle lifting unit and the second lifting unit may move along the extension direction of the connection component 1. For example, the driving component may include a motor and a driving subunit disposed between the middle lifting unit and the first lifting unit. The driving component may further include another motor and another driving subunit disposed between the second lifting unit and the middle lifting unit. The driving subunit may include but is not limited to a worm-rack drive, a gear-rack drive, a screw-nut drive, a belt drive, a chain drive, etc. In some embodiments, the driving component may drive the middle lifting unit and/or the first lifting unit to move to lift the support component. The lifting assembly may realize multi-stage expansion and contraction during lifting the lifting assembly from an extended state to a contracted state, thereby reducing the size of the lifting assembly in a storage state, reducing the size of the C-arm 110, and increasing a number of application scenarios of the C-arm 110.

In some embodiments, at least one of the first support component 2, the second support component 3, or the connection component 1 may include a chamber 6. The driving component (e.g., the driving assembly, the first driving unit 4, the second driving unit 5, etc.) may be disposed in the chamber 6 of the connection component 1. Alternatively or additionally, one or more wires or cables used by one or more units disposed in the first support component 2 and one or more units disposed in the second support component 3 may pass through the chamber 6. The disposition of the chamber 6 may reduce the weight and material usage of the C-arm 110. It should be noted that a number or a count of the chamber 6 of each of at least one of the first support component 2, the second support component 3, and the connection component 1 may be one or multiple (e.g., 2, 3, 4, 6, etc.), and the multiple chambers 6 may be communicated with each other. Those skilled in the art may determine the number, arrangement, size, and shape of the chamber 6 according to an actual need. For example, a cross-sectional shape of the chamber 6 may include a circle, a square, a polygon, an irregular shape, etc. Such modifications are still within the protection scope of the present disclosure.

In the present disclosure, a material of at least one of the first support component 2 and the second support component 3 may include carbon fiber. For example, the first support component 2 and/or the second support component 3 may be integrally formed using carbon fiber. Carbon fiber refers to a fibrous carbon material with a carbon content of more than 90%. Carbon fiber may have low density, high strength, and high rigidity. In some embodiments, the material of the first support component 2, the second support component 3, or the connection component 1 may include but is not limited to glass fiber, metal fiber, aluminum alloy, magnesium alloy, titanium alloy, porous ceramic, horse stainless steel, plastic steel, etc.

In some embodiments, one or more reinforcing ribs may be disposed on at least one of the first support component or the second support component. The reinforcing ribs may further improve the structural strength of the first support component 2 and/or the second support component 3 without increasing a wall thickness of the first support component 2 and/or the second support component 3, thereby preventing the first support component 2 and/or the second support component 3 from being deformed by force, and improving support performance of the first support component 2 and/or the second support component 3 for the one or more units (e.g., the one or more first units, the one or more second units, etc.) disposed thereon. It should be noted that a shape of the reinforcing rib(s) may include a stripe shape, a grid shape, etc. Those skilled in the art may determine the shape of the reinforcing rib(s) according to an actual need, which is not limited in the present disclosure. In some embodiments, to improve the structural strength of the C-arm 110, one or more reinforcing ribs may be disposed in the connection component 1. In some embodiments, the reinforcing rib(s) may be disposed on an outer surface of one or more components (e.g., the first support component 2, the second support component 3, the connection component 1, etc.) of the C-arm 110. The reinforcing rib(s) may be used to improve the rigidity of the C-arm 110, and those skilled in the art may dispose the reinforcing rib(s) on other positions, and the number or the count of the reinforcing rib(s) may be determined based on an actual need. In some embodiments, the reinforcing rib(s) may include other rigid-reinforced structures, such as a reinforcing plate, a reinforcing stiffener, or the like, or any combination thereof. Such variation and modification are still within the protection scope of the present disclosure. Alternatively, a material of the connection component 1 may include carbon fiber. In some alternative embodiments, the connection component 1, the first support component 2, and the second support component 3 may also be formed by splicing sheet metal parts or castings.

Figure 5:
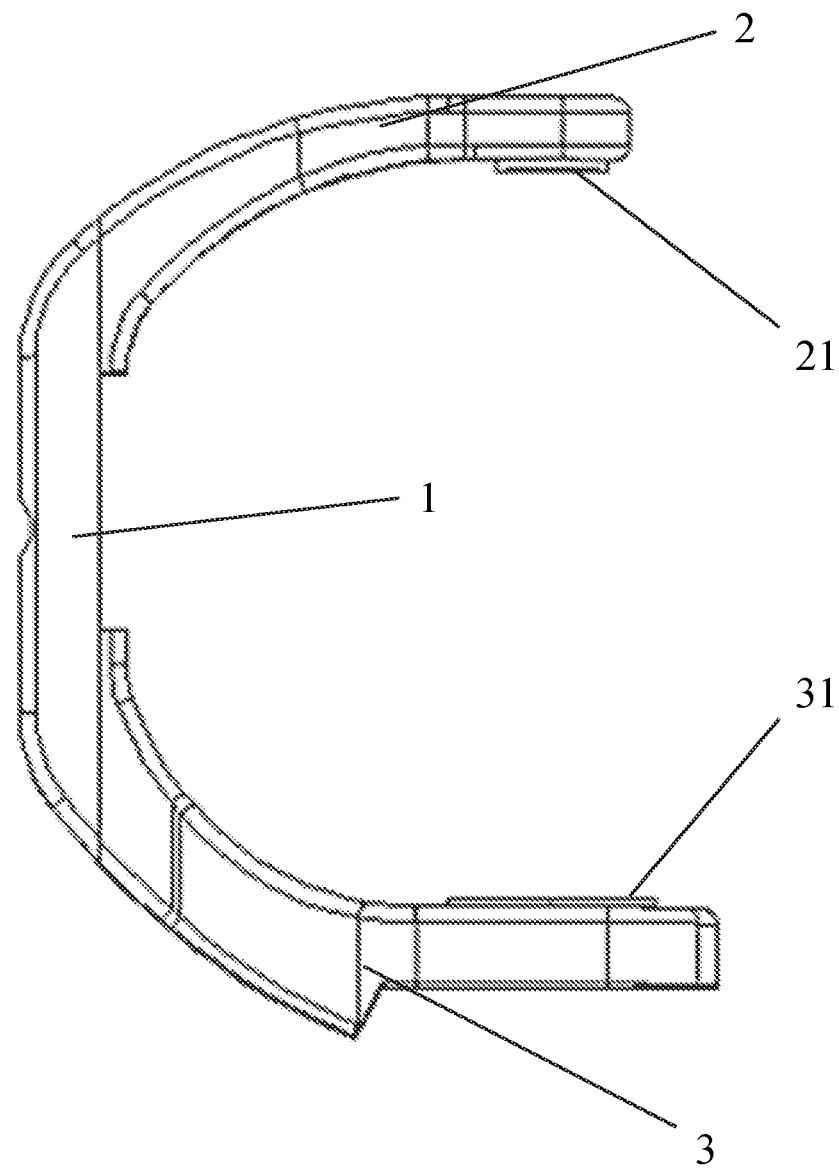
FIG. 5 is a schematic diagram illustrating a three-dimensional structure of an exemplary C-arm according to some embodiments of the present disclosure.
Figure 6:
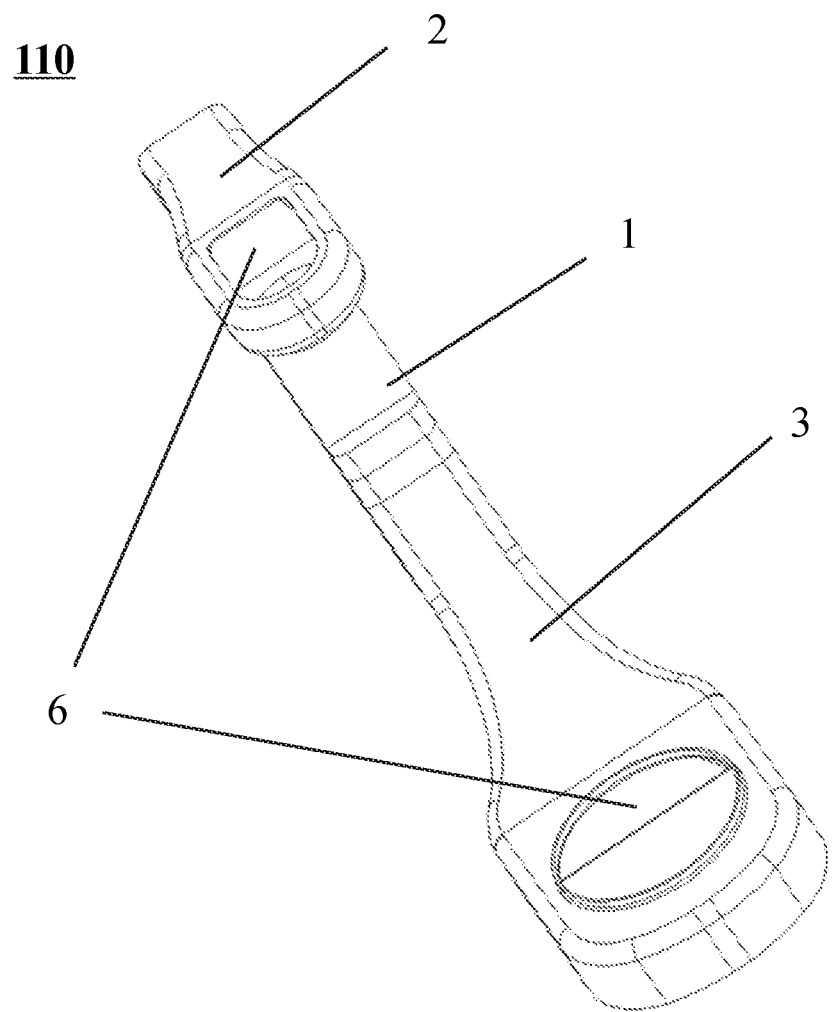
FIG. 6 is a schematic diagram illustrating a three-dimensional structure of an exemplary C-arm according to some embodiments of the present disclosure.
Figure 7:
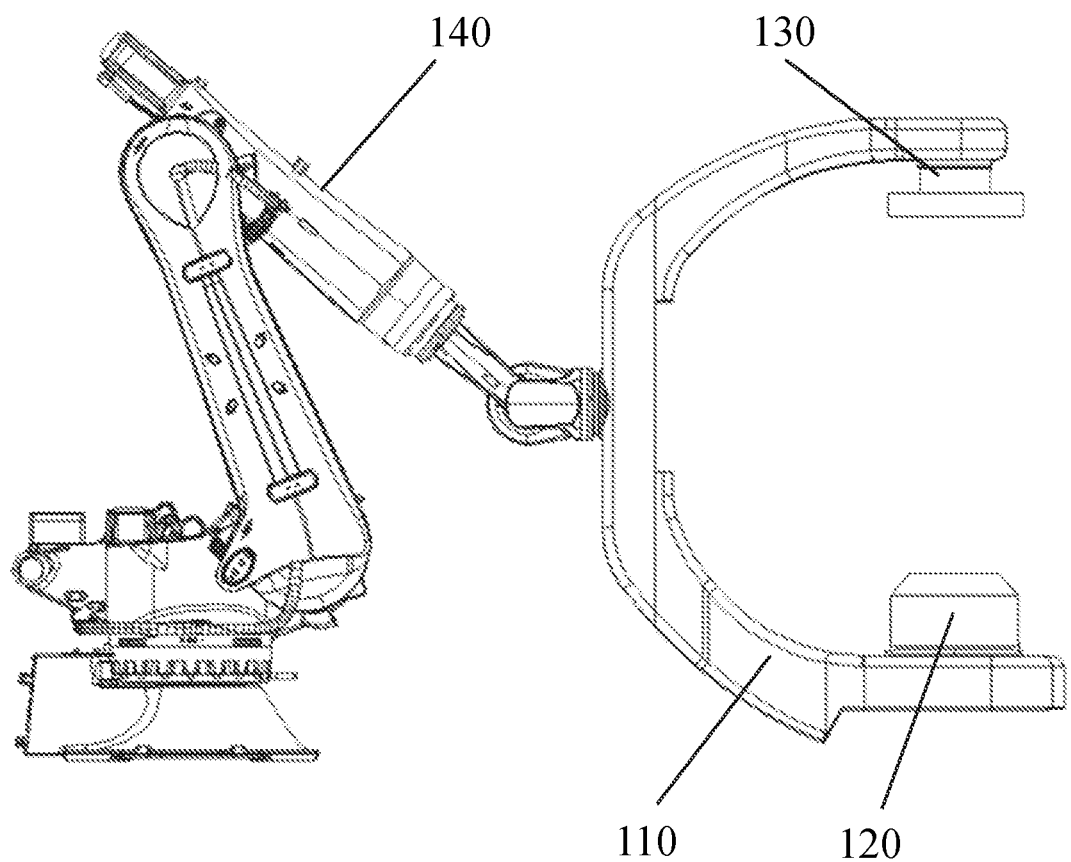
FIG. 7 is a schematic diagram illustrating a three-dimensional structure of an exemplary X-ray device according to some embodiments of the present disclosure.

FIG. 5 is a schematic diagram illustrating a three-dimensional structure of a C-arm according to some embodiments of the present disclosure. FIG. 6 is another perspective view of the three-dimensional structure of the C-arm as illustrated in FIG. 5.

As shown in FIG. 5 and FIG. 6, the C-arm 110 may include a connection component 1, a first support component 2, and a second support component 3. The first support component 2 and the second support component 3 may be connected to two ends of the connection component 1, respectively. Each of the first support component 2 and the second support component 3 may be integrally formed of carbon fiber. The connection component 1, the first support component 2, and the second support component 3 may be connected and formed a C shape. Carbon fiber refers to a fibrous carbon material with a carbon content of more than 90%. Carbon fiber may have low density, high strength, and high rigidity. The first support component 2 and the second support component 3 may be integrally formed, thereby effectively preventing a connection between the first support component 2 and the second support component 3 from breaking, and improving the structural strength of the first support component 2 and the second support component 3. In actual use, each of the first support component 2 and the second support component 3 may be configured to support one or more other components (e.g., a radiation generator of an X-ray device, a radiation detector of an X-ray device, etc.). The connection component 1 may be configured to connect the first support component 2 to the second support component 3, and the connection component 1 may be connected to a gantry body (e.g., the gantry of the X-ray device 1000). In some embodiments, an integral molding process of the first support component 2 and/or the second support component 3 may include but is not limited to a wet layup molding, a liquid molding, a compression molding, etc. For example, the integral molding process of the first support component 2 and/or the second support component 3 may include three steps. In the first step, the carbon fiber may be attached to a mold. In the second step, a mold clamping, a curing, and a demolding operation may be performed. In the third step, the first support component 2 and/or the second support component 3 may be integrally formed.

In some embodiments, the connection component 1 may be integrally formed of carbon fiber. After the first support component 2, the second support component 3, and the connection component 1 are respectively integrated formed and manufactured, the integrally formed first support component 2, the integrally formed second support component 3, and the integrally formed connection component 1 may be assembled, that is, the C-arm 110 may have a three-segment structure. In some embodiments, a connection manner of the connection component 1 and the first support component 2 and/or a connection manner of the connection component 1 and the second support component 3 may include but is not limited to a flange connection, a bolt connection, a snap connection, or the like, or any combination thereof. In some embodiments, positions of the first support component 2, the second support component 3, and the connection component 1 may be adjusted according to an actual need (e.g., a power of the radiation generator on the X-ray device) during an installation process of the C-arm 110, thereby improving the general adaptability of the C-arm 110. For example, the connection component 1 may include a plurality of positions that may be connected to the first support component 2 and/or the second support component 3.

In some embodiments, at least one of the first support component 2 and the second support component 3 may be integrally formed with the connection component 1. For example, one of the first support component 2 and the second support component 3 may be integrally formed with the connection component 1 to generate an integrally formed structure, and the integrally formed structure may be assembled with the other one of the first support component 2 and the second support component 3. As another example, the first support component 2, the second support component 3, and the connection component 1 may be integrally formed together. In some alternative embodiments, the connection component 1 may be formed by combing a plurality of parts, and the plurality of parts may include one or more metal parts (e.g., a sheet metal part, a casting, a forging, etc.). A combination mode of the plurality of parts may be various. For example, the combination mode of the plurality of parts may include a weld mode, a bond mode, etc. As another example, the combination mode of the plurality of parts may include a rivet mode, a bolt mode, a snap mode, etc. In some alternative embodiments, the connection component 1 may be integrally formed of a metal.

In some embodiments, the first support component 2 may include a first connection unit 21. The first connection unit 21 may be connected to a radiation generator. The second support component 3 may include a second connection unit 31. The second connection unit 31 may be connected to a radiation detector. At least one of the first connection unit 21 and the second connection unit 31 may include but are not limited to a threaded connection component, a clamp connection component, a flange connection component, a rivet connection component, etc. For example, the first connection unit 21 and/or the second connection unit 31 may include one or more through holes or threaded holes, and the radiation generator and/or the radiation detector may be connected to the C-arm 110 through a threaded connection part (e.g., a nut, a bolt, etc.). As another example, the first connection unit 21 and/or the second connection unit 31 may include a clamping slot or a clamping hole, and the radiation generator and/or the radiation detector may be clamped to the C-arm 110 via the clamping slot or the clamping hole.

The C-arm disclosed in the present disclosure may include one or more of the following exemplary beneficial effects: (1) a driving assembly may drive a first support component and a second support component to move toward or away from each other along an extending direction of a connection component, thereby adjusting a distance between a radiation generator and a radiation detector, reducing the load of a carrying mechanism of the C-arm during the movement of the first support component and the second support component, and reducing a load change of a carrying mechanism of the C-arm; (2) a first driving unit may drive the first support component to move relative to the connection component, and a second driving unit may drive the second support component to move relative to the connection component, thereby improving efficiency of adjusting the distance between the first support component and the second support component, and improving convenience and efficiency of performing an operation such as a medical examination or a medical treatment on a patient; (3) a load of the connection component of the C-arm and the load of the carrying mechanism of the C-arm may be reduced during the movement of the first support component and the second support component 3; (4) a position change of the center of gravity of the C-arm may be reduced or the position of the center of gravity of the C-arm may be constant, thereby improving the efficiency of controlling the movement of the C-arm; (5) the strength and rigidity of the C-arm may be improved and the weight of the C-arm may be reduced; (6) the support efficiency of the first support component for one or more first units disposed on the first support component and the support efficiency of the second support component and one or more second units disposed on the second support component may be improved; (7) manufacturing and transportation costs of the C-arm may be reduced; (8) The efficiency of adjusting the distance between the first support component and the second support component may be improved, thereby adjusting the operation space between the first support component and the second support component; (9) the efficiency of adjusting the position of the radiation generator may be improved, and accordingly a region of the patient needed to be imaged or treated may be accurately positioned. It should be noted that different embodiments may have different beneficial effects. In different embodiments, the beneficial effects may include any of the beneficial effects mentioned above or any other beneficial effects that may be realized.

The present disclosure provides an X-ray device according to some embodiments of the present disclosure. As shown in FIG. 1 to FIG. 4 and FIG. 7, the X-ray device 1000 may include a gantry 140, a radiation generator 120, a radiation detector 130, and the C-arm 110 as described according to the aforementioned embodiments. A connection component 1 of the C-arm 110 may be rotatably connected to the gantry 140. For example, the connection component 1 of the C-arm 110 may be connected to the gantry 140 via a bearing. A driving component may be disposed on the C-arm 110, and the driving component may be configured to drive the C-arm 110 to rotate relative to the gantry 140. A position of the radiation generator 120 may be adjusted during a process of an X-ray image of a patient performed by the X-ray device 1000, thereby improving the efficiency and accuracy of positioning the patient. A first support component 2 and a second support component 3 may move relative to the connection component 1, thereby improving the efficiency of adjusting a distance between the radiation generator 120 and the radiation detector 130 of the X-ray device 1000 including the C-arm 110, and improving the convenience of performing X-ray examination on the patient.

In some embodiments, the connection component 1 may move relative to the gantry 140. The movement of the connection component 1 relative to the gantry 140 may be controlled, thereby reducing a torque generated by the connection component 1 and one or more units disposed on the connection component 1 and performed on the gantry 140, and prolonging the service life of the gantry 140. In some embodiments, two ends of the connection component 1 may be connected to the radiation generator 120 and the radiation detector 130, respectively. A weight of the radiation generator 120 may be greater than that of the radiation detector 130. When a middle portion of the connection component 1 is fixedly connected to the gantry 140, a rotational torque of an end of the connection component 1 connected to the radiation generator 120 applied to the gantry 140 may be greater than a rotational torque of the other end of the connection component 1 connected to the radiation detector 130 applied to the gantry 140, which will affect the stability of the connection between the gantry 140 and the connection component 1. In some embodiments, a third driving component may be disposed on the gantry 140, and the third driving component may drive the connection component 1 to move relative to the gantry 140, thereby reducing the rotational torque generated by the connection component 1 and the one or more units disposed on the connection component 1 applied to the gantry 140. In some embodiments, the connection component 1 may move along an extending direction of the connection component 1. In some embodiments, a controller may control the connection component 1 to move when the controller adjusts a source to image receptor distance (SID) of the X-ray device 1000. In some embodiments, the controller may control the connection component 1 to move after that the controller adjusts the SID. In some embodiments, a torque sensor may be disposed on the connection component 1. The torque sensor may be configured to detect rotational torque information of the connection between the connection component 1 and the gantry 140 and send the rotational torque information to the controller. The controller may determine whether to control the movement of the connection component 1 based on the rotational torque information. For example, the controller may determine whether to control the movement of the connection component 1 based on whether the rotation torque is within a preset range. In some embodiments, the third driving component may be the same as or similar to the second driving unit and/or the first driving unit described in the foregoing embodiments. For example, the third driving component may include a motor and a driving unit (e.g., a worm-rack drive, a gear-rack drive, a screw-nut drive, a belt drive, a chain drive, etc.).

In some embodiments, the gantry 140 may include a robot arm, and the robot arm may be configured to control rotation and a position of the C-arm, thereby expanding the application of the gantry 140. In some embodiments, the robot arm may include a flexible robot arm or a rigid robot arm with multiple degrees of freedom. The flexible robot arm may include a lightweight elastic rod, and the lightweight elastic rod may be configured to realize a bend of the flexible robot arm. The flexible robot arm may include an octopus arm, an elephant trunk, and other bionic robotic arms. In some embodiments, the rigid robot arm may include one or more rigid links and one or more discrete joints. In some embodiments, the X-ray device 1000 may include a digital subtraction angiography (DSA) device. A DSA refers to an X-ray device that combines angiography and computer image processing technology, which may improve the clearness of images of the blood vessels and lesions of a patient.

It will be apparent to those skilled in the art that various changes and modifications can be made in the present disclosure without departing from the spirit and scope of the disclosure. In this manner, the present disclosure may be intended to include such modifications and variations if the modifications and variations of the present disclosure are within the scope of the appended claims and the equivalents thereof.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure, or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures, or characteristics may be combined as suitable in one or more embodiments of the present disclosure.

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claim subject matter lies in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate a certain variation (e.g., ±1%, ±5%, ±10%, or ±20%) of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable. In some embodiments, a classification condition used in classification is provided for illustration purposes and modified according to different situations. For example, a classification condition that "a probability value is greater than the threshold value" may further include or exclude a condition that "the probability value is equal to the threshold value."

We claim:

1. A C-arm, comprising a connection component, a driving component, a first support component, and a second support component, wherein
    the first support component is configured to support a radiation generator,
    the second support component is configured to support a radiation detector,
    the first support component and the second support are movably connected to the connection component, and
    the driving component is configured to drive a movement of the first support component relative to the connection component.

2. The C-arm of claim 1, wherein
    the driving component includes a driving assembly, and
    the driving assembly is configured to drive the first support component and the second support component to move toward or away from each other.

3. The C-arm of claim 2, wherein
    the driving assembly drives the first support component to move at a first speed, the driving assembly drives the second support component to move at a second speed, and the first speed is the same as the second speed.

4. The C-arm of claim 2, wherein
    the driving assembly drives the first support component to move at a third speed, the driving assembly drives the second support component to move at a fourth speed, and the third speed is different from the fourth speed.

5. The C-arm of claim 4, wherein
    a ratio of the third speed to the fourth speed is equal to a ratio of weights of the second support component and one or more second units disposed on the second support component to weights of the first support component and one or more first units disposed on the first support component.

6. The C-arm of claim 4, wherein
    a position of a center of gravity of the C-arm during movements of the first support component and the second support component relative to the connection component is constant.

7. The C-arm of claim 2, wherein
    the driving assembly includes a motor, a worm, a first rack, and a second rack,
    the motor drives the worm to rotate, an axis of the worm being along the extending direction of the connection component,
    the worm includes a first spiral segment and a second spiral segment, and a spiral direction of the first spiral segment is opposite to a spiral direction of the second spiral segment,
    the first rack is engaged with the first spiral segment and connected to the first connection component, and
    the second rack is engaged with the second spiral segment and connected to the second connection component.

8. The C-arm of claim 7, wherein a lead of the first spiral segment is different from a lead of the second spiral segment.

9. The C-arm of claim 2, wherein
    the driving assembly includes a motor, a leadscrew, a first nut, and a second nut,
    the motor drives the leadscrew to rotate along an axis of the leadscrew, an axis of the leadscrew being along the extending direction of the connection component,
    the leadscrew includes a third spiral segment and a fourth spiral segment, and a spiral direction of the third spiral segment is opposite to a spiral direction of the fourth spiral segment,
    the first nut is matched with the third spiral segment and connected to the first connection component, and
    the second nut is matched with the second spiral segment and connected to the second connection component.

10. The C-arm of claim 2, wherein
    the driving assembly includes a motor, a gear, a third rack, and a fourth rack,
    the motor drives the gear to rotate,
    the third rack and the fourth rack are disposed along the direction of the extending direction of the connection component and meshes with the gear, and the third rack is connected to the first support component and the fourth rack is connected to the second support component.

11. The C-arm of claim 1, wherein
the driving component includes a first driving unit and a second driving unit,
the first driving unit is configured to drive the first support component to move relative to the connection component, and
the second driving unit is configured to drive the second support component to move relative to the connection component.

12. The C-arm of claim 11, wherein
the first support component moves relative to the connection component along a first route,
the second support component moves relative to the connection component along a second route, and
the first route is parallel to or collinear with the second route.

13. The C-arm of claim 11, comprising a controller, wherein
the controller is configured to control the first driving unit to drive the first support component to move, and/or
the controller is configured to control the second driving unit to drive the second support component to move.

14. The C-arm of claim 13, wherein
the controller controls the first support component to move relative to the connection component at a seventh speed,
the controller controls the second support component to move relative to the connection component at an eighth speed, and
the seventh speed is different from the eighth speed.

15. The C-arm of claim 11, wherein
the first driving unit or the second driving unit includes a motor and at least one of a worm-rack drive, a gear-rack drive, a screw-nut drive, a belt drive, or a chain drive.

16. The C-arm of claim 1, wherein
at least one of the first support component, the second support component, or the connection component includes a chamber, and the driving component is disposed in the chamber.

17. The C-arm of claim 1, wherein
the first support component and the second support component are made of a material selected from carbon fiber, glass fiber, or metal fiber.

18. The C-arm of claim 17, wherein
one or more reinforcing ribs are disposed on at least one of the first support component or the second support component.

19. An X-ray device, comprising a gantry, a radiation generator, a radiation detector, and a C-arm, wherein the C-arm comprises a connection component, a driving component, a first support component, and a second support component, and wherein
the first support component is configured to support a radiation generator,
the second support component is configured to support a radiation detector,
the first support component and the second support are movably connected to the connection component,
the driving component is configured to drive a movement of the first support component relative to the connection component, and
the connection component of the C-arm is rotatably connected to the gantry.

20. A C-arm, comprising a connection component, a first support component, and a second support component, wherein
the first support component is configured to support a radiation generator,
the second support component is configured to support a radiation detector,
the first support component is connected to a first end of the connection component,
the second support component is connected to a second end of the connection component, and
each of the first support component and the second support component is integrally formed of a material selected from carbon fiber, glass fiber, or metal fiber.

* * * * *